United States Patent
Marion

(10) Patent No.: US 6,840,917 B2
(45) Date of Patent: Jan. 11, 2005

(54) IMPLANTABLE SUBCUTANEOUS VALVE FOR THE TREATMENT OF HYDROCEPHALUS, AND ADJUSTING DEVICES THEREFOR

(76) Inventor: Bernard Marion, La Grande Maison, Mont-Dol (FR), 35120

( * ) Notice: Subject to any disclaimer, the term of this patent is extended or adjusted under 35 U.S.C. 154(b) by 410 days.

(21) Appl. No.: 09/986,983

(22) Filed: Nov. 13, 2001

(65) Prior Publication Data

US 2002/0058901 A1 May 16, 2002

(30) Foreign Application Priority Data

Nov. 13, 2000 (FR) .............................................. 00 14551

(51) Int. Cl.[7] .......................... A61M 5/00; F16K 31/12
(52) U.S. Cl. ................................ 604/9; 604/8; 251/35; 137/519.5
(58) Field of Search ..................... 604/8–10; 137/519.5, 137/329.03, 385, 15.22; 251/65, 315.1

(56) References Cited

U.S. PATENT DOCUMENTS

| | | | |
|---|---|---|---|
| 3,288,142 A | 11/1966 | Hakim | 128/350 |
| 3,527,226 A | 9/1970 | Hakim | 128/350 |
| 4,443,214 A | 4/1984 | Marion | 604/9 |
| 4,673,384 A | 6/1987 | Marion | 604/10 |
| 4,676,772 A * | 6/1987 | Hooven | 604/9 |
| 5,637,083 A * | 6/1997 | Bertrand et al. | 604/9 |
| 5,643,194 A * | 7/1997 | Negre | 604/8 |
| 6,371,464 B1 * | 4/2002 | Porche et al. | 267/166.1 |

FOREIGN PATENT DOCUMENTS

| | | |
|---|---|---|
| EP | 0 060 369 | 9/1982 |
| EP | 0 421 557 | 4/1991 |
| FR | 2 721 520 | 12/1995 |

* cited by examiner

Primary Examiner—Angela D. Sykes
Assistant Examiner—Leslie Deak
(74) Attorney, Agent, or Firm—Jacobson Holman PLLC

(57) ABSTRACT

The invention relates to a subcutaneous valve having opening pressure that can be adjusted non-invasively from the outside, said valve comprising a body presenting a chamber with a cylindrical inside side wall, an inlet duct and an outlet duct for cerebospinal fluid both opening out in said side wall, a valve member such as a ball placed at the inside end of said inlet duct, a spring blade fitting closely to the side wall of said chamber and urging the valve member against its seat, and a moving member controlled from the outside and provided with means for locking it in a determined position, the length of the spring blade acting on the valve member being determined by the position of said moving member. The valve is remarkable in that said moving member is constituted by a resilient flexible arcuate blade fitting closely to the cylindrical inside wall of said chamber. The valve is applicable to the treatment of hydrocephalus.

20 Claims, 3 Drawing Sheets

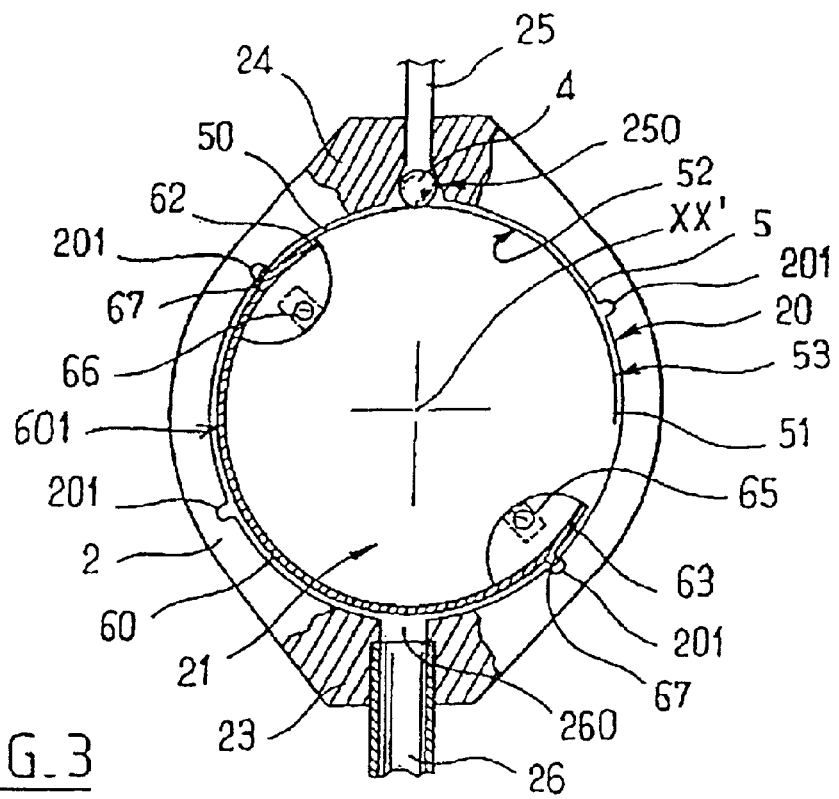
FIG_3
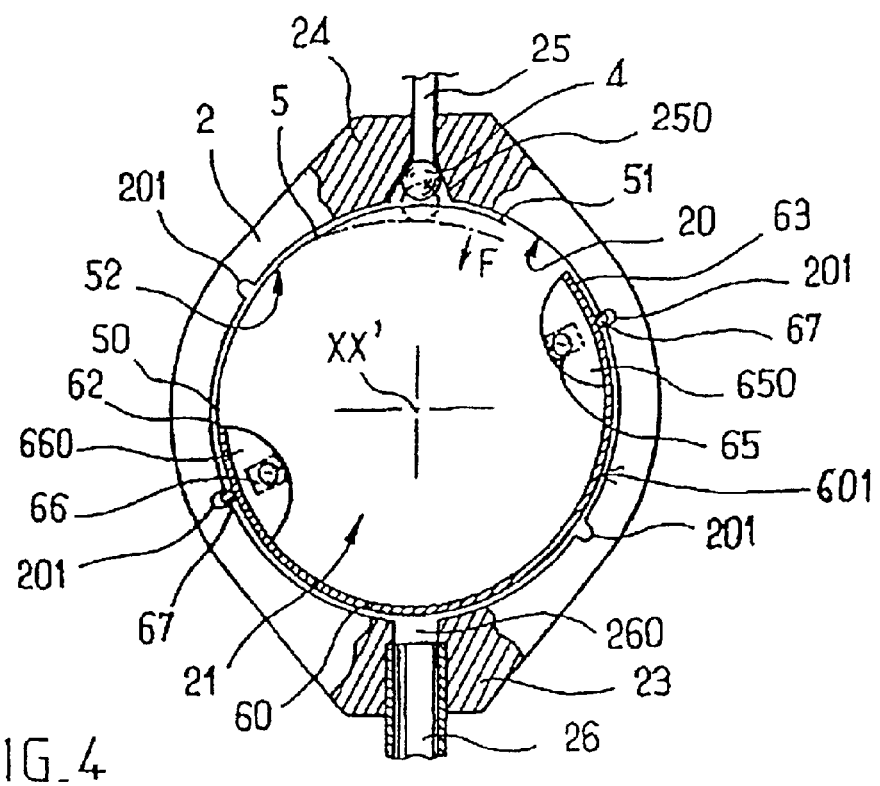
FIG_4

IMPLANTABLE SUBCUTANEOUS VALVE FOR THE TREATMENT OF HYDROCEPHALUS, AND ADJUSTING DEVICES THEREFOR

The present invention relates to surgically-implantable valves used for the treatment of hydrocephalus by regulating cerebrospinal fluid (CSF), and it also relates to a device for adjusting the opening pressure of said valve from the outside, i.e. through skin tissue.

BACKGROUND OF THE INVENTION

It has been known for more than fifty years that one of the major causes of hydrocephalus is a disturbance or blockage of the natural sites for resorbing CSF, namely the arachnoid villosities.

In normal adults, the brain is maintained at a constant hydrostatic pressure inside the cranial cavity by means of the self-adjusting mechanism of the arachnoid villosities that open and close appropriately to maintain a constant pressure gradient inside the cerebral ventricles. As a result, any disturbance in CSF resorption will simultaneously give rise to an increase in the volume of the cerebral ventricles, and in most cases to an increase in intraventricular pressure.

In newborns whose frontanelles are still open, hydrocephalus is attended by an increase in the volume of the skull caused by the increase in intraventricular pressure.

In adults, because the skull is rigid, hydrocephalus is revealed by disorders in gait control, incontinence, mental disorders, and a gradual deterioration of the cerebral parenchyma.

A known method of treating hydrocephalus consists in diverting CSF from the cerebral ventricles to some other resorption site such as the heart or the peritoneum.

To do this, a "proximal" or "ventricular" catheter is introduced into one of the ventricles of the cranial cavity by trepanning the patient's skull, and this catheter is connected to a "distal" or drainage catheter which is inserted under the scalp and leads either to the heart or to the peritoneum.

The purpose of the arachnoid villosities is to maintain a constant pressure difference between the CSF and venous blood so as to avoid ventricles being drained off while in the orthostatic position. Thus, when a drainage catheter is installed, it is necessary for the proximal catheter under the scalp to include a pressure-regulating valve intended to restore the proper pressure gradient inside the cranial cavity.

Several types of valve have already been proposed, such as those of US patents Nos. U.S. Pat. Nos. 3,288,142 and 3,527,226 in which the pressure-regulating valve includes a liquid-pressure regulating device that consists in a spherical ball co-operating with a conical seat, said ball being held in place by a pre-calibrated spring so as to open at a preset pressure. Unfortunately, that type of valve responds at a single predetermined pressure difference only, which means that a complete series of valves must be provided to a neurosurgical department to make it possible to operate on the variety of pressure ranges that is consistent with the various cases of hydrocephalus that are to be treated. Furthermore, it is to be expected that during evolution of the disease, a previously-implanted valve will be set to open at a pressure that becomes too high or, on the contrary, too low. In either case the valve must be replaced, thus involving another operation.

To solve that problem, a programmable valve as described in European patent No. EP 0 060 369 (U.S. Pat. No. 4,443,214) discloses the possibility of adjusting opening pressure from the outside in "non-invasive" manner so that the valve can be caused to open at a pressure desired by the neurosurgeon, as a function of the physiological condition of the patient.

That programmable valve consists in a valve body of flat cylindrical shape with two opposite projections respectively constituting inlet and outlet ducts for CSF flow. At the inner end of the inlet duct, a frustoconical seat is provided for engaging a corresponding spherical ball which is urged against its seat by a curved spring blade extending along a portion of the inside wall of the valve body. One end of the curved spring blade is fastened to the end of a diametrally-extending rotary magnetic bar (or "rotor").

The neurosurgeon can make use of an outside magnet acting through the scalp of the patient and the wall of the valve to turn the magnetic bar into a desired position. In other words, by turning the magnetic bar, the length of the active portion of the spring blade which acts on the spherical ball can be varied, thereby enabling the valve opening pressure to be adjusted.

The rotor and the spring blade are immobilized by indexing means which act between the end of the rotor bar and the inside of the valve body, thereby providing a plurality of indexed positions corresponding to different preset opening pressures.

Such immobilization of the rotor is entirely satisfactory in most cases, however some very powerful magnetic fields, such as those used in nuclear magnetic resonance (NMR) procedures, can change the position of the rotor. Therefore, after performing such a procedure, the position of the rotor must be checked on the patient and readjusted if it is found to have changed.

Another drawback of the valve described above is the diametral position of the rotor which extends across the valve body, i.e. across the flow of CSF, thus to some extent impeding the free flow of fluid through the valve from its inlet duct to its outlet duct.

Furthermore, it is known that in hydrocephalus, the protein content of CSF increases and can sometimes reach as much as 2% by weight (2 grams (g) per hundred grams) or even more, as reported in the literature. As a consequence, as soon as a valve presents one or more internal sites where it can retain CSF, the risks of clogging increase.

To solve the problem of the position of the rotor possibly changing under the effect of a powerful magnetic field, a subcutaneous valve has been proposed as described in patent No. FR 2 721 520.

That valve has features similar to those of the valve described in EP 0 060 369, except that the magnetic rotor consists of an H-shaped bar in which the two pairs of side branches on either side of the central axis of rotation act as means for guiding two micromagnets. These two micromagnets have facing faces of the same polarity, and are suitable for sliding between the branches of said rotor along the longitudinal axis of the bar so as to actuate locking pins which are suitable for co-operating with a series of cavities provided in the cylindrical side face of the valve chamber.

That valve solves the drawback of a possible unexpected change in the rotor position, i.e. in spring position, in the event of a patient being subjected to a strong unidirectional magnetic field, since when one of the two magnets is attracted towards the center of the valve, the other magnet is repelled a little harder into its cavity. As a consequence, both micromagnets cannot be removed simultaneously from their respective cavities.

However, because that device has two sliding parts inside the valve, the number of potential fluid-retaining or "dead" sites is further increased, particularly since the mechanism needs to be extremely miniaturized in order to be integrated in a valve chamber having inside dimensions of centimeter (cm) order. Such a valve therefore risks clogging even more quickly than the valve of document EP 0 060 369.

OBJECTS AND SUMMARY OF THE INVENTION

The object of the present invention is therefore to resolve the above-mentioned drawbacks of providing a valve in which the position of the spring is not modified even when the valve is subjected to a strong magnetic field, and which also improves CSF flow inside the valve chamber.

To this end, the invention relates to a subcutaneous valve for the treatment of hydrocephalus, said valve having an opening pressure that can be adjusted non-invasively from the outside, the valve comprising a valve body presenting an internal chamber having a cylindrical side wall, an inlet duct and an outlet duct for cerebospinal fluid, both ducts opening out in the side wall of said chamber and being suitable for connection respectively to an ventricular catheter and to a drainage catheter for said fluid, a valve member such as ball mounted on a seat at the inside end of said inlet duct, a curved spring blade fitting closely against the side wall and urging the valve member against its seat, a magnetic moving member movable in rotation about an axis X-X' under control from outside the valve, and means for locking said moving member in a determined position, the length of the active portion of the spring blade acting on the valve member being determined by the position of said moving member.

According to the invention, said moving member is constituted by a resilient flexible arcuate blade fitting closely to the cylindrical inside wall of said chamber over at least a fraction of the circumference thereof, while exerting pressure thereon, said arcuate blade being shaped so as to avoid impeding the flow of fluid through said chamber into the outlet duct.

As a result, the moving member is immobilized by a balanced distribution of contact points between the arcuate blade and the inside wall of the valve chamber, thus avoiding any unbalanced immobilization as can result from the single fixing point provided at the end of the rotor-forming bar in EP 0 060 369.

In addition, the valve of the present invention provides better CSF flow inside the chamber since the rotor-forming bar which used to extend across the chamber as described in EP 0 060 369 is omitted.

According to other advantageous and non-limiting features of the invention:
one of the ends of the spring blade is fixed to the cylindrical wall of said chamber, its other end being free, and one of the ends of the arcuate blade can slide over the inside face (referenced 52 in FIG. 2) of said spring blade, bearing thereagainst in order to exert pressure thereon;
one of the ends of the spring blade is fixed to one of the ends of the arcuate blade, the other end of the spring blade being free;
the arcuate blade has an opening for allowing the fluid that is inside the internal chamber to pass towards the outlet duct;
the spring blade occupies at least one-third of the inside circumference of said chamber; and the means for locking the moving member comprise at least two detents suitable for being received in at least two corresponding cavities, said detents being disposed diametrically opposite each other on the outside face of the arcuate blade and the corresponding cavities being formed in the inside side wall of said chamber, or vice versa.

In a first embodiment, the arcuate blade carries two micromagnets on its inside face, the micromagnets being fixed to respective ends of the arcuate blade on opposite sides of the vertical axis of rotation X-X' and themselves being disposed vertically so that they have respective same-sign poles lying in a common plane and facing upwards.

Alternatively, in a second embodiment, the arcuate blade carries two micromagnets on its inside face, the micromagnets being fixed to respective ends of the arcuate blade on opposite sides of the vertical axis of rotation X-X' and themselves being disposed vertically so that they have respective opposite-sign poles lying in a common plane and facing upwards.

The invention also provides a device for externally adjusting the opening pressure of the above valve. The version of that device which is described below corresponds to the above-specified first embodiment of the invention.

The device consists in two separate magnets arranged and oriented in such a manner that: i) they have same-sign poles in the same plane; ii) said sign is opposite to the signs of the two micromagnets of the arcuate blade; and iii) the distance l between the poles is slightly shorter than the distance/ between the poles of the micromagnets of the arcuate blade. The magnets of the device are much stronger than the micromagnets, thus causing them to retract the arcuate blade into the inside of the chamber, thereby enabling the arcuate blade to be turned.

In two advantageous variants of the adjustment device, it comprises:
two magnets embedded in a resin disk and disposed in such a manner that their respective same-sign poles lie in a common plane and face downwards, being of opposite sign to the sign of the poles of the micromagnets of the arcuate blade; and
two magnets embedded in a resin disk and disposed in such a manner that their respective opposite-sign poles lie in a common plane and face downwards, being of opposite signs to the signs of the poles of the micromagnets of the arcuate blade.

The invention also provides a device for externally identifying the position of the arcuate blade by using a compass having a non-magnetic needle.

BRIEF DESCRIPTION OF THE DRAWINGS

Other features and advantages of the invention will appear on reading the following description of a preferred embodiment of the invention. This description refers to the accompanying drawings, in which:

FIG. 3 is a plan view, partially in section, showing the valve of the invention;

FIG. 4 is a view similar to FIG. 3, with the valve adjusted to a different opening pressure.

MORE DETAILED DESCRIPTION

Figure 1:
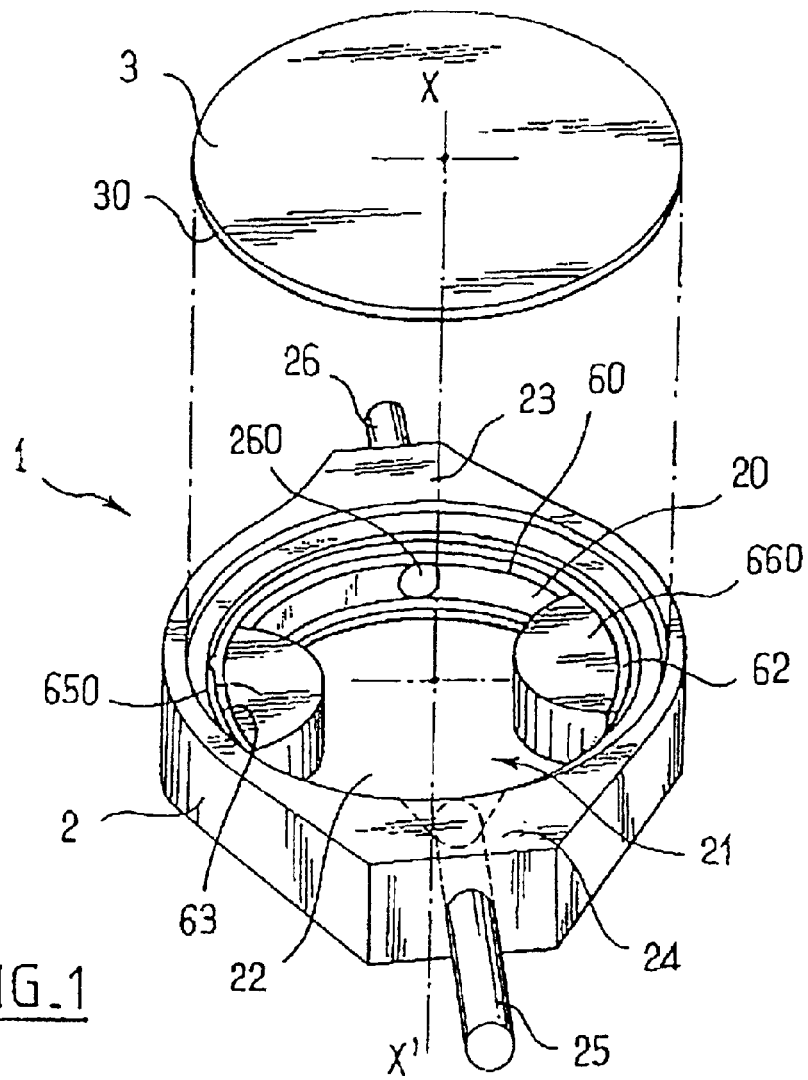
FIG. 1 is an exploded perspective view of a valve of the invention.

The valve shown in FIG. 1 comprises a valve body 1 constituted by a cylindrical box 2 which is closed by a cover 3.

The valve has an axis passing perpendicularly through the center of the cover 3, and represented by a line X-X'.

The box 2 and its cover 3 are advantageously made of a biocompatible material, so that the valve can be implanted.

The subcutaneous valve presents a thin cylindrical internal chamber 21 formed between the bottom 22 of the box, the cylindrical side wall 20 thereof, and its top cover 3.

The box 2 presents two diametrically-opposite extensions 23 and 24 each having a respective inlet or outlet duct 25 or 26 for CSF formed therein. These two ducts open out in the cylindrical side wall 20 of the chamber via respective diametrically-opposite orifices 250 and 260.

As can be seen better in FIGS. 3 and 4, the inside end 250 of the inlet duct 25 is frustoconical in shape, thereby defining a seat for receiving a ball 4 which constitutes a valve member.

The ball 4 is held against its seat 250 by a curved spring blade 5 that fits closely to the shape of the cylindrical side wall 20 of the chamber 21. Advantageously, the spring blade 5 extends over at least one-third of the inside circumference of said chamber 21.

As can be seen better in FIG. 2, the spring blade 5 is fixed in a cantilevered position via one of its ends 50 to a moving member 6 which is described below, while the other end 51 of the spring blade is left free.

The moving member 6 comprises an arcuate blade 60 which is flexible, resilient, and made of a plastics material or a metal. This arcuate blade 60 has an inside face 600 facing towards the inside of the chamber 21, an opposite outer face 601, and two opposite ends given respective references 62 and 63, the end 62 being the end fixed to the end 50 of the spring blade 5. This arcuate blade 60 is placed inside the internal chamber 21 so that its outer face 601 matches the shape of the cylindrical inside wall 20 of said chamber, and so that said arcuate blade is pressed against said wall 20 and exerts a certain amount of pressure thereon.

The arcuate blade 60 extends over the inside end 260 of the outlet duct 26 and it presents a longitudinal opening 64 for facilitating the flow of CSF from the inside of the chamber 21 into the outlet duct 26.

The arcuate blade 60 also carries two micromagnets 65 and 66 on its inside face 600, said magnets being placed to face each other. Each micromagnet 65, 66 is embedded in a mass of biocompatible plastics material respectively referenced 650, 660, and secured to the inside face 600 of the blade 60.

Figure 2:
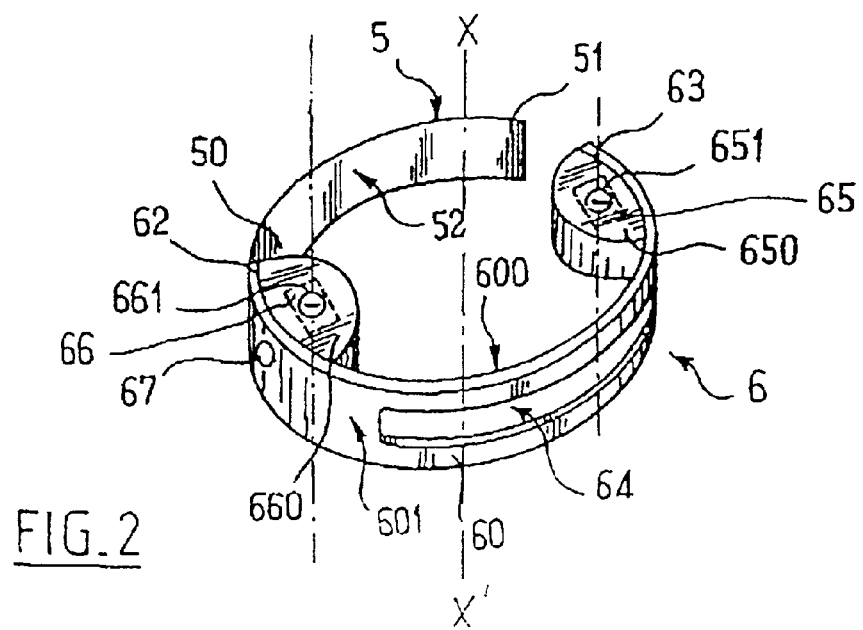
FIG. 2 is a perspective view of the moving member of the valve.

In a first embodiment as shown in FIG. 2, the two micromagnets have their respective same-sign poles 651 and 661 lying in a common upwardly-facing plane. As shown in FIG. 2, these two poles are negative, but they could equally well be positive.

This particular disposition of the magnets with same-sign poles lying in the same plane makes it possible to avoid the untimely turning effect which is inevitable when both poles belong to a single magnet and are therefore of opposite signs, particularly under the effect of a very strong magnetic field such as that used in NMR procedures.

By means of an external adjustment device that is described below, it is possible to act on the said micromagnets 65 and 66 from outside the valve to cause the arcuate blade 60 to turn about the central axis X-X' of the internal chamber. This central axis X-X' thus also constitutes an axis of rotation for the moving member 6.

Finally, as can be seen in FIGS. 2 to 4, the arcuate blade 60 has means for locking it in a predetermined position. These means comprise at least two detents for being received in at least two corresponding cavities.

In the embodiment shown in FIGS. 3 and 4, the outer face 601 of the arcuate blade 60 carries two detents 67 projecting from the plane of said face and located in diametrically-opposite positions. The inside wall 20 of the chamber 21 presents four cavities 201 of a shape that is substantially complementary to the shape of the detents 67.

By using these locking means, the moving member 6 can be immobilized in two different positions corresponding to two different pressures being applied by the spring blade 5 on the ball 4.

When the moving member 6 is in the position shown in FIG. 4, the point of contact between the spring blade 5 and the ball 4 is remote from the point where the spring 5 is fixed to the end 62 of the arcuate blade 60, such that the movement exerted by the spring opposing thrust exerted by the fluid on the ball 4 is small. As a result, the opening pressure of the valve is low when the arcuate blade is in this position.

In contrast, when the moving member 6 is in the position shown in FIG. 3, the point of contact between the spring blade 5 and the ball 4 is close to the point where the blade 5 is fixed to the end 62 of the arcuate blade 60, so the spring opposes a much larger force. As a result, in this position of the arcuate blade, the opening pressure of the valve is high.

The position of the moving member 6 serves to adjust the opening pressure of the subcutaneous valve, and thus the intraventricular pressure of the patient.

For simplification purposes, FIGS. 3 and 4 show only two sets of two cavities 201 for two different positions of the arcuate blade. Nevertheless, it is quite possible to provide a larger number of such cavities so as to increase the number of adjustment positions.

In addition, the resilient nature of the arcuate blade 60 enables it to behave like a spring and to press itself against the cylindrical wall 20. This ensures that the moving member 60 is immobilized more securely.

The flow of fluid is also greatly improved since there is no longer any obstacle in the middle of the chamber 21, as used to be the case with a bar-shaped rotor.

In a second embodiment which is not shown in the figures, the spring blade 5 has its end 50 fixed to the cylindrical wall 20 of the internal chamber, while its other end 51 is free. The spring blade 5 is also disposed in the configuration shown in FIG. 4 so that its free end 51 is close to the seat 250. Furthermore, the arcuate blade 60 is disposed in such a manner that its end 62, and in particular the plastics material block 660 can slide over the inside face 52 of the spring blade 5, bearing thereagainst so as to exert pressure thereon. Under such circumstances, it the position of the end 62 of the arcuate blade 60 which determines the opposing force applied by the spring blade 5.

Figure 5:
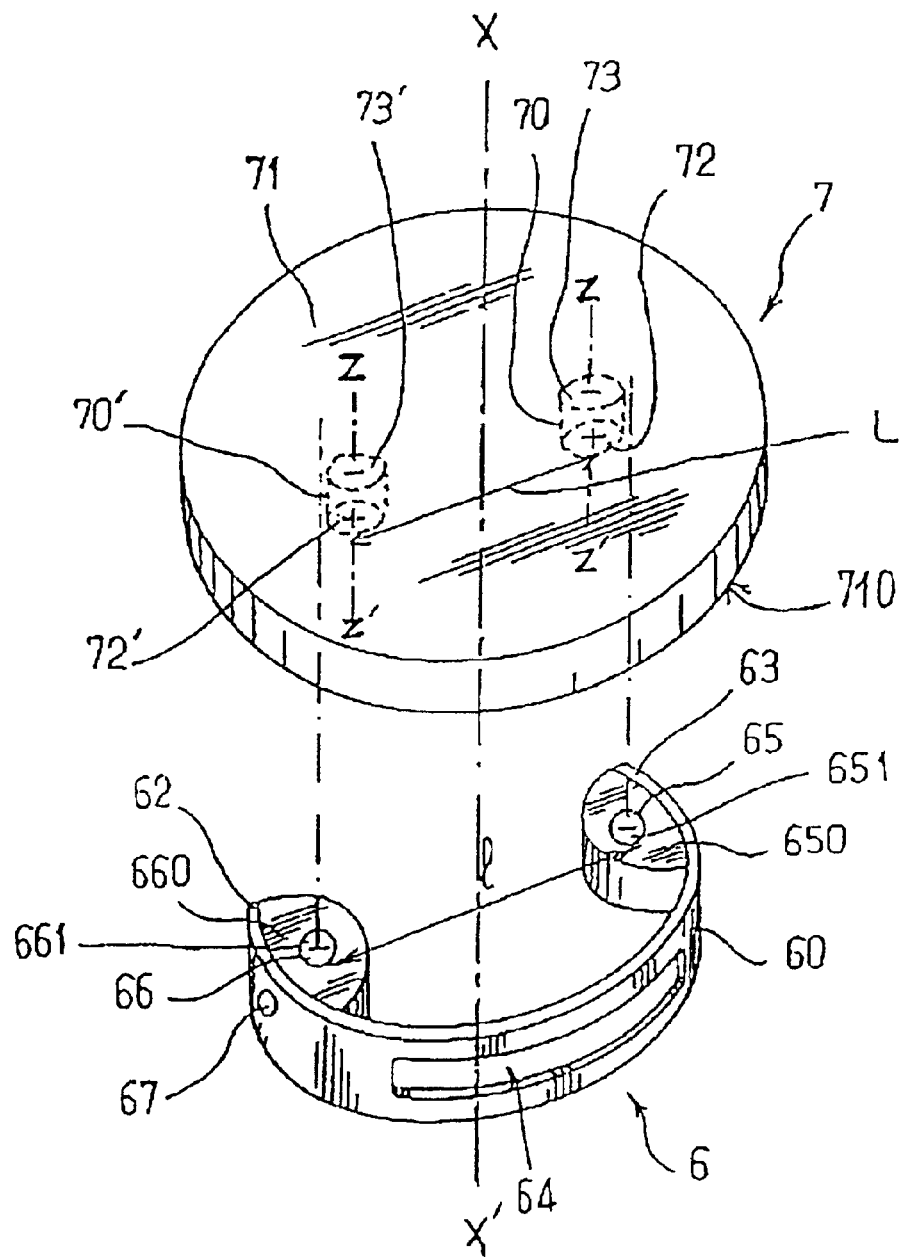
FIG. 5 is a perspective view of the arcuate portion of the valve and also showing an embodiment of the adjustment device of the invention.

The arcuate blade 60 is turned by means of an external adjustment device, and an embodiment thereof referenced 7 is shown in FIG. 5. For simplification purposes, this figure does not show the spring blade 5.

As can be seen in this figure, the adjustment device 7 comprises two strong cylindrical magnets 70 and 70' embedded in a support such as a disk of resin 71, for example. These magnets are disposed vertically in the disk, i.e.

perpendicularly to its plane 710, but in such a manner as to present same-sign poles lying in the plane of the disk. As can be seen in FIG. 5, their positive poles are pointed downwards because the two facing poles of the two micromagnets to which they are presented are negative poles.

The spacing between the two magnets of the adjustment device is determined so that the distance L between their respective axes Z and Z' is slightly smaller than the distance l between the axes of the two micromagnets of the arcuate blade.

To adjust the opening pressure of the valve, the device 7 is placed on the patient's head over the site of the valve so that the two positive poles 72 and 72' of the magnets of the adjustment device overlie the two negative poles of the two micromagnets of the arcuate blade. Given the above-specified characteristics, the two poles of the magnet of the adjustment device cause the two ends of the arcuate blade to be retracted away from the inside wall 20, such that any turning of the device then enables the arcuate blade to be moved into a desired position, and simultaneously moves the spring blade 5 relative to the ball 4.

In the event of the two micromagnets 65 and 66 of the arcuate blade having upwardly directed positive poles, then the two magnets 70 and 70' of the adjustment device should be inverted through 180° so as to bring their respective negative poles 73 and 73' into register with the two positive poles of the micromagnets 65 and 66.

Finally, when the two micromagnets 65 and 66 have respective poles of opposite signs pointing upwards, then the adjustment device 7 should be identical to that described with reference to FIG. 5 except that one only of its two magnets should be inverted through 180°.

In order to determine the position of the arcuate blade inside the valve after it has been implanted, it is possible to use a compass that is ordinary except insofar as its needle is made of soft iron that is not magnetized. Any implanted valve is easily found beneath the skin of the patient because of the small projection it produces in the scalp. By applying the compass to the site containing the valve, the needle immediately indicates the position of one of the two micromagnets of the arcuate blade, thus indicating the position of the arcuate blade itself.

What is claimed is:

1. A subcutaneous valve for the treatment of hydrocephalus, said valve having an opening pressure that can be adjusted non-invasively from the outside, the valve comprising a valve body presenting an internal chamber having a cylindrical side wall, an inlet duct and an outlet duct for cerebrospinal fluid, both ducts opening out in the side wall of said chamber and being suitable for connection respectively to a ventricular catheter and to a drainage catheter for said fluid, a valve member including a ball, mounted on a seat within said chamber at the opening of said inlet duct, a curved spring blade fitting closely against the side wall of said chamber and urging the ball against said seat, a magnetic moving member movable in rotation about a vertical axis under control from outside the valve, and means for locking said moving member in a determined position, a length of an active portion of the spring blade acting on the valve member being determined by the position of said moving member, said moving member constituted by a resilient flexible arcuate blade fitting closely to the cylindrical inside wall of said chamber over at least a fraction of an inside circumference thereof, while exerting pressure thereon, said arcuate blade being shaped so as to avoid impeding the flow of fluid through said chamber into the outlet duct.

2. A subcutaneous valve according to claim 1, wherein a first end of the spring blade is fixed to the cylindrical wall of said chamber, a second end thereof being free, and wherein a first end of the arcuate blade can slide over an inside face of said spring blade, bearing thereagainst in order to exert pressure thereon.

3. A subcutaneous valve according to claim 1, wherein a first end of the spring blade is fixed to a first end of the arcuate blade, a second end of the spring blade being free.

4. A subcutaneous valve according to claim 1, wherein the arcuate blade has an opening for allowing the fluid that is inside the internal chamber to pass towards the outlet duct.

5. A subcutaneous valve according to claim 1, wherein the spring blade occupies at least one-third of the inside circumference of said chamber.

6. A subcutaneous valve according to claim 1, wherein the means for locking the moving member comprise at least two detents suitable for being received in at least two corresponding cavities, said detents being disposed diametrically opposite each other on an outside face of the arcuate blade and the corresponding cavities being formed in the inside side wall of said chamber, or vice versa.

7. A subcutaneous valve according to claim 1, wherein the arcuate blade carries two micromagnets on an inside face thereof, the micromagnets being fixed to respective ends of the arcuate blade on opposite sides of the vertical axis of rotation, said magnets being disposed vertically so as to have respective same-sign poles lying in a common plane and facing upwards.

8. A subcutaneous valve according to claim 1, wherein the arcuate blade carries two micromagnets on an inside face thereof, the micromagnets being fixed to respective ends of the arcuate blade on opposite sides of the vertical axis of rotation, said magnets being disposed vertically so as to have respective opposite-sign poles lying in a common plane and facing upwards.

9. A subcutaneous valve according to claim 7, further comprising a magnetic device for externally adjusting said valve, said device including two magnets embedded in a resin disk and disposed in such a manner that respective same-sign poles thereof lie in a common plane and face downwards, being of opposite sign to the sign of the poles of the micromagnets of the arcuate blade.

10. A subcutaneous valve according to claim 8, further comprising a magnetic device for externally adjusting said valve, said device including two magnets embedded in a resin disk and disposed in such a manner that respective opposite-sign poles thereof lie in a common plane and face downwards, being of opposite signs to the signs of the poles of the micromagnets of the arcuate blade.

11. A subcutaneous valve for the treatment of hydrocephalus, said valve comprising:
- a valve body with an internal chamber having a cylindrical side wall, an inlet duct and an outlet duct, both ducts opening out in said side wall;
- a valve member mounted on a valve seat in said chamber at the opening of said inlet duct;
- a curved spring blade fitting against said side wall of said chamber and having an active portion urging said valve member against said seat;
- a resilient flexible arcuate blade fitting against the cylindrical side wall of said chamber over at least a fraction of a circumference thereof while exerting pressure thereon, said arcuate blade being rotatably movable along said circumference, a length of said active portion of said spring blade being determined by a rotated position of said arcuate blade along said circumference;

a magnetic element fixed to said arcuate blade for effecting said rotating movement from outside said valve; and a locking element for locking said arcuate blade in a determined position.

12. A subcutaneous valve according to claim 11, wherein a first end of the spring blade is fixed to the cylindrical wall of said chamber and a second end thereof is free, such that a first end of the arcuate blade can slide over an inside face of said spring blade, bearing thereagainst in order to exert pressure thereon.

13. A subcutaneous valve according to claim 11, wherein a first end of the spring blade is fixed to a first end of the arcuate blade, a second end of the spring blade being free.

14. A subcutaneous valve according to claim 11, wherein the arcuate blade has an elongated opening for allowing the fluid that is inside the chamber to pass towards the outlet duct.

15. A subcutaneous valve according to claim 11, wherein the arcuate blade fits closely to the cylindrical side wall along at least half of said circumference.

16. A subcutaneous valve according to claim 11, wherein the locking element includes at least two detents suitable for being received in at least two corresponding cavities, said detents being disposed diametrically opposite each other on an outside face of the arcuate blade and the corresponding cavities being formed in the cylindrical side wall of said chamber, or vice versa.

17. A subcutaneous valve according to claim 11, wherein said magnetic element includes two micromagnets on an inside face of said arcuate blade, said micromagnets being fixed to respective ends of the arcuate blade on opposite sides of a vertical axis of rotation thereof, said micromagnets being disposed vertically with respective same-sign poles lying in a common plane and facing upwards.

18. A subcutaneous valve according to claim 11, wherein said magnetic element includes two micromagnets on an inside face of said arcuate blade, said micromagnets being fixed to respective ends of the arcuate blade on opposite sides of a vertical axis of rotation thereof, said micromagnets being disposed vertically with respective opposite-sign poles lying in a common plane and facing upwards.

19. A subcutaneous valve according to claim 17, further comprising a magnetic device for externally adjusting said valve, said device including two magnets embedded in a resin disk and disposed in such a manner that respective same-sign poles thereof lie in a common plane and face downwards, being of opposite sign to the sign of the poles of the micromagnets of the arcuate blade.

20. A subcutaneous valve according to claim 18, further comprising a magnetic device for externally adjusting said valve, said device including two magnets embedded in a resin disk and disposed in such a manner that respective opposite-sign poles thereof lie in a common plane and face downwards, being of opposite signs to the signs of the poles of the micromagnets of the arcuate blade.

* * * * *

UNITED STATES PATENT AND TRADEMARK OFFICE
CERTIFICATE OF CORRECTION

PATENT NO. : 6,840,917 B2
DATED : January 11, 2005
INVENTOR(S) : Bernard Marion

It is certified that error appears in the above-identified patent and that said Letters Patent is hereby corrected as shown below:

Column 4,
Lines 28-29, change "and (iii) the distance l between the poles is slightly shorter than the distance/" to -- and (iii) the distance L between the poles is slightly shorter than the distance l --

Signed and Sealed this

Twenty-fourth Day of May, 2005

JON W. DUDAS
*Director of the United States Patent and Trademark Office*